US010231620B2

(12) United States Patent
Ishiai et al.

(10) Patent No.: US 10,231,620 B2
(45) Date of Patent: Mar. 19, 2019

(54) OPHTHALMIC APPARATUS (71) Applicant: KABUSHIKI KAISHA TOPCON, Tokyo (JP)

(72) Inventors: Ryota Ishiai, Tokyo (JP); Kota Fujii, Toda (JP); Shigeru Okikawa, Tokyo (JP)

(73) Assignee: KABUSHIKI KAISHA TOPCON, Itabashi-ku, Tokyo (JP)

( * ) Notice: Subject to any disclaimer, the term of this patent is extended or adjusted under 35 U.S.C. 154(b) by 0 days.

(21) Appl. No.: 15/514,609

(22) PCT Filed: Aug. 28, 2015

(86) PCT No.: PCT/JP2015/074492
§ 371 (c)(1),
(2) Date: Mar. 27, 2017

(87) PCT Pub. No.: WO2016/052034
PCT Pub. Date: Apr. 7, 2016

(65) Prior Publication Data
US 2017/0224213 A1    Aug. 10, 2017

(30) Foreign Application Priority Data

Sep. 30, 2014    (JP) ................. 2014-201311

(51) Int. Cl.
*A61B 3/14*    (2006.01)
*A61B 3/10*    (2006.01)
(Continued)

(52) U.S. Cl.
CPC .............. *A61B 3/14* (2013.01); *A61B 3/0041* (2013.01); *A61B 3/10* (2013.01); *A61B 3/102* (2013.01);
(Continued)

(58) Field of Classification Search
CPC ....... A61B 3/14; A61B 3/0016; A61B 3/0075; A61B 3/102; A61B 3/117; A61B 3/12;
(Continued)

(56) References Cited

U.S. PATENT DOCUMENTS

2013/0194094 A1* 8/2013 Nakahara ................. A61B 3/14
340/540
2013/0258286 A1* 10/2013 Iwase ................... A61B 3/0041
351/208
(Continued)

FOREIGN PATENT DOCUMENTS

JP    2008073099 A    4/2008
JP    2010-224101    * 10/2010
(Continued)

OTHER PUBLICATIONS

International Search Report and Written Opinion dated Apr. 7, 2016 in connection with International Patent Application No. PCT/JP2015/074492, 7 pgs.

*Primary Examiner* — Jordan Schwartz
(74) *Attorney, Agent, or Firm* — Chiesa Shahinian & Giantomasi PC (57) ABSTRACT

An ophthalmic apparatus capable of selectively performing a first imaging mode in which imaging of a subject's eye is performed in a first state where an attachment unit is not attached, and a second imaging mode in which imaging of the subject's eye is performed in a second state where the attachment unit is attached. The ophthalmic apparatus includes: an operation unit; an attachment state determination unit to determine whether or not the attachment unit is attached; a correspondence determination unit to determine whether or not the correspondence between the imaging mode designated by a use of the operation unit and an attachment state of the attachment unit obtained by the attachment state determination unit is appropriate; and a (Continued)

controller to perform control for prohibiting imaging in at least the designated imaging mode when the correspondence determination unit has determined that the correspondence is not appropriate.

9 Claims, 7 Drawing Sheets (51) Int. Cl.
*A61B 3/117* (2006.01)
*A61B 3/12* (2006.01)
*A61B 3/00* (2006.01)
*A61B 3/18* (2006.01)

(52) U.S. Cl.
CPC ............... *A61B 3/117* (2013.01); *A61B 3/12* (2013.01); *A61B 3/185* (2013.01)

(58) Field of Classification Search
CPC ........ G02B 15/02; G02B 15/04; G02B 15/06; G02B 15/08; G02B 15/10; G02B 15/12; G03B 17/14
USPC .............. 359/672–675; 396/72–73, 422, 544
See application file for complete search history.

(56) References Cited

U.S. PATENT DOCUMENTS

2013/0258349 A1\* 10/2013 Makihira ........... G01B 9/02015
356/497
2013/0286348 A1\* 10/2013 Makihira ............... A61B 3/102
351/206

FOREIGN PATENT DOCUMENTS

JP 2013212314 A 10/2013
JP 2014138904 A 7/2014

\* cited by examiner

OPHTHALMIC APPARATUS

CROSS-REFERENCE TO RELATED APPLICATIONS

This application is a U.S. national phase filing under 35 U.S.C. § 371 of PCT Application No. PCT/JP2015/074492, filed Aug. 28, 2015, and claims priority thereto under 35 U.S.C. § 119 to Japanese Patent Application No. 2014-201311, filed Sep. 30, 2014, the entireties of both of which are incorporated by reference herein.

FIELD

Embodiments described herein relate generally to an ophthalmic apparatus.

BACKGROUND

Various apparatuses are used in the ophthalmic field. For example, apparatuses for acquiring images of a subject's eye (imaging apparatus), apparatuses for examining a subject's eye (examination apparatus), and the like are used. Examples of imaging apparatuses include an optical coherence tomography (OCT, hereafter) apparatus, a fundus camera, a slit lamp microscope, a scanning laser ophthalmoscope (SLO), and the like. Examples of examination apparatuses include a refractometer, a keratometer, a tonometer, a perimeter, and the like. Further, multifunctional apparatuses, which are combinations of two or more apparatuses, are also used.

Some ophthalmic apparatuses include a light source for illuminating an anterior segment (cornea, etc.) of a subject's eye at a position deviated from the main optical path for imaging or examination. There are also various kinds of ophthalmic apparatuses to which attachment units for optionally employing predetermined functions are attached. A typical attachment unit includes an optical system disposed between a subject's eye and an optical system for imaging or examination.

However, with a conventional ophthalmic apparatus, a predetermined imaging function corresponding to an attachment unit has been realized by switching an imaging mode according to an attachment state of or to a type of the attachment unit. For this reason, when imaging has been performed in an imaging mode that does not correspond to the attachment state of or to the type of the attachment unit, it has not been possible to perform desired imaging, which requires additional imaging.

SUMMARY

An object of the present invention is to provide a technology for preventing a situation in which a subject's eye is imaged in an inappropriate imaging mode.

An ophthalmic apparatus according to one embodiment is configured to be capable of selectively performing imaging in a first imaging mode and a second imaging mode. The first imaging mode is an imaging mode in which imaging of a subject's eye is performed in a first state where an attachment unit is not attached. The second imaging mode is an imaging mode in which imaging of a subject's eye is performed in a second state where the attachment unit is attached. The ophthalmic apparatus according to one embodiment includes the followings: an operation unit configured for designating an imaging mode; an attachment state determination unit configured to determine whether or not the attachment unit is attached; a correspondence determination unit configured to determine whether or not the correspondence between the imaging mode designated by the use of the operation unit and an attachment state of the attachment unit obtained by the attachment state determination unit is appropriate; and a controller configured to perform control for prohibiting imaging in at least the designated imaging mode when the correspondence determination unit has determined that the correspondence is not appropriate.

An ophthalmic apparatus according to another embodiment is configured to perform imaging of a subject's eye in a state in which two or more attachment units corresponding to two or more imaging modes are selectively attached. The ophthalmic apparatus according to another embodiment includes the followings: an operation unit configured for designating an imaging mode; a type specification unit configured to specify a type of an attachment unit attached; a correspondence determination unit configured to determine whether or not the correspondence between the imaging mode designated by the use of the operation unit and the type of the attachment unit obtained by the type specification unit is appropriate; and a controller configured to perform control for prohibiting imaging in at least the designated imaging mode when the correspondence determination unit has determined that the correspondence is not appropriate.

According to the embodiments, it is possible to prevent a situation in which the subject's eye is imaged in an inappropriate imaging mode.

DETAILED DESCRIPTION

Referring now to the drawings, exemplary embodiments of an ophthalmic apparatus according to the present invention are described below. The following embodiment describes an example of an ophthalmic apparatus configured to acquire both OCT images of a subject's eye and of a fundus. For acquiring the OCT images of the subject's eye, the ophthalmic apparatus uses Fourier domain OCT (more specifically, spectral domain OCT). Such an ophthalmic apparatus is similar to the apparatus disclosed in Japanese Unexamined Patent Application Publication No. 2008-73099. The following embodiment is capable of acquiring both OCT images of a fundus and of an anterior segment. The ophthalmic apparatus according to the following embodiment may further include a function of an ophthalmic examination apparatus for examining the subject's eye.

In the following embodiment, the ophthalmic apparatus acquires images of the subject's eye corresponding to an attachment unit by switching an imaging mode according to an attachment state of or to a type of the attachment unit. However, embodiments are not limited thereto. The following embodiment images a desired site of the subject's eye in the imaging mode corresponding to the attachment state of or to the type of the attachment unit. Examples of the attachment unit includes an optical attachment unit having one or more optical elements placed on the front side of an objective lens, and a face support (forehead rest, chin rest, or the like) attachment unit for placing the face of the subject at a suitable position. The following embodiment describes mainly the example that uses optical attachment units.

Figure 1:
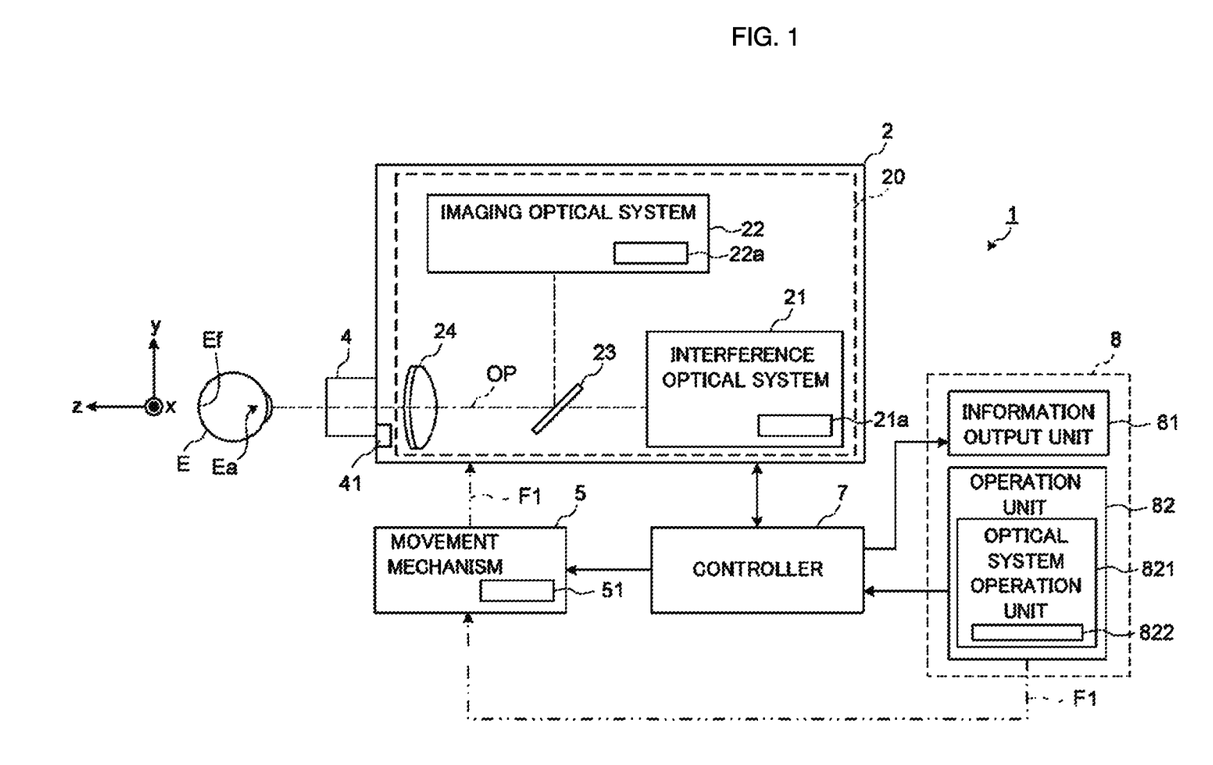
FIG. 1 is a schematic diagram illustrating an example of the configuration of an ophthalmic apparatus according to an embodiment.

FIG. 1 shows an example of the configuration of the ophthalmic apparatus according to the first embodiment. The ophthalmic apparatus 1 has a function of imaging the subject's eye E. In particular, the ophthalmic apparatus 1 has a function of imaging a fundus Ef of the subject's eye E and a function of imaging an anterior segment Ea. The ophthalmic apparatus 1 includes an optical unit 2, a movement mechanism 5, a controller 7, and a user interface 8. The ophthalmic apparatus 1 may also include an attachment unit 4 that is configured to be attachable to the optical unit 2.

The optical unit 2 includes an optical system 20 for imaging the subject's eye E. The optical system 20 includes various kinds of optical elements for imaging the subject's eye E. Further, the optical unit 2 may include a mechanism for moving and/or rotating an optical element included in the optical system 20. The optical system 20 includes an interference optical system 21 and an imaging optical system 22.

As with general OCT apparatuses, the interference optical system 21 includes the following components: a light source (a low coherence light source, a wavelength tunable light source, etc.); a fiber coupler that splits light output from the light source into measurement light and reference light, and that superposes the measurement light returning from the subject's eye E on the reference light; a device for changing the length of the optical path for OCT measurement (the optical path of the measurement light and/or the optical path of the reference light); various kinds of optical elements such as a focusing lens for changing the focal position of the interference optical system 21; and a detector (a spectroscope, a balanced photo detector, or the like) that detects interference light generated by the fiber coupler. In such a case, the ophthalmic apparatus 1 includes a circuit and/or a processor that forms a cross sectional images, a three-dimensional image, etc. of the subject's eye E (the fundus Ef, the anterior segment Ea, etc.) based on the detection result of the interference light obtained by the detector.

As with general fundus cameras, the imaging optical system 22 includes the following components: various kinds of lenses (a focusing lens, an imaging lens, a focusing lens, a relay lens, etc.); optical elements other than lenses (a diaphragm); and image sensors (a CCD image sensor, a CMOS image sensor, etc.). The imaging optical system 22 may also include a light source, which emits infrared light (near-infrared light) and/or visible light, for example.

The imaging optical system 22 may include two or more cameras. For example, two cameras are provided at different positions on the front surface (the surface facing the subject) of the optical unit 2. The two cameras photograph the anterior segment Ea at different directions from each other. In other words, the two cameras perform stereoscopic imaging of the anterior segment Ea. The ophthalmic apparatus 1 can obtain the position information of the anterior segment Ea based on the two images substantially simultaneously acquired by the two cameras.

In the configuration example shown in FIG. 1, the optical unit 2 stores the optical system 20 inside. In the optical system 20, the optical path extending from the interference optical system 21 and the optical path extending from the imaging optical system 22 are combined by a beam splitter 23. The beam splitter 23 is, for example, a dichroic mirror or a half mirror. The beam splitter 23 is an optical element according to the wavelength band used for the interference optical system 21 and to the wavelength band used for the imaging optical system 22. An objective lens 24 is disposed on the combined optical path OP formed by the beam splitter 23.

The attachment unit 4 is attached to the front surface of the optical unit 2. FIG. 1 shows a state in which the attachment unit 4 is attached. As shown, the attachment unit 4 is disposed between the objective lens 24 and the subject's eye E. An attachment unit detector 41 is provided on the part (or in the vicinity thereof) of the optical unit 2 to which the attachment unit 4 is attached. The attachment unit detector 41 detects attachment state of the attachment unit 4. "Detection of attachment state" includes, for example, any one or both of detection of an arbitrary event and/or detection of an arbitrary state related to the attachment of the attachment unit 4. Examples of the detection of the event and/or the state include the followings: detection of the fact that the attachment unit 4 has been attached; detection of the fact that the attachment unit 4 is now being attached; detection of the fact that the attachment unit 4 has been detached; detection of the fact that the attachment unit 4 is now been detached. For example, the attachment unit detector 41 is configured to detect the attachment state of the attachment unit 4 in response to variation of a predetermined physical quantity generated according to attachment (or detachment) of the attachment unit 4. Examples of the physical quantity include the magnitude and direction of magnetic field and the magnitude of pressure (or presence or absence of the application of pressure). The attachment unit detector 41 has a configuration according to the type of the physical quantity to be detected. The attachment unit detector 41 includes, for example, a magnetic sensor, a pressure sensor, a micro switch, or the like. Further, the attachment unit 4 includes additional components according to the type of the physical quantity to be detected. For example, the attachment unit 4 includes a magnet, a convex portion, a concave portion, or the like.

The attachment unit 4 may be, for example, an optical attachment unit for anterior segment imaging to carry out OCT for the anterior segment Ea by the use of the interference optical system 21. Such attachment unit 4 includes at least a lens for focusing the measurement light output from the interference optical system 21 on the anterior segment Ea (cornea, etc.). The lens functions so as to focus the measurement light, originally to be focused on the fundus Ef, on the anterior segment Ea.

The movement mechanism 5 is a mechanism for moving the optical unit 2. The movement mechanism 5 moves the optical unit 2 at least in the front-rear direction (the ±z direction). However, the movable direction of the optical unit 2 is not limited to the front-rear direction. The optical unit 2 moves electrically and/or manually. In the case of electric movement, the movement mechanism 5 includes an actuator 51. The actuator 51 includes, for example, a pulse motor. The actuator 51 generates a driving force under the control of the controller 7. The movement mechanism 5 includes a mechanism that transmits the driving force output from the actuator 51 to the optical unit 2. Here, the controller 7 automatically controls the actuator 51 according to a predetermined computer program(s). Alternatively, the controller 7 controls the actuator 51 based on operation signals from an operation unit 82 of the user interface 8. On the other hand, in the case of manual movement, the actuator 51 is not required. In the case of manual movement, a user performs an operation for moving the optical unit 2 by the use of the operation unit 82. A force F1, which is applied through this operation, is transmitted to the movement mechanism 5 via a mechanism (not shown). The movement mechanism 5 converts the transmitted force F1 into a force F2 that is for moving the optical unit 2.

Further, the interference optical system 21 includes a movement mechanism 21a that is for moving, in the optical axis direction of the interference optical system 21, a first focusing lens (not shown) that changes the focal position of the interference optical system 21. The first focusing lens includes one or more lenses. The first focusing lens moves electrically and/or manually. In the case of electric movement, the movement mechanism 21a includes an actuator. The actuator includes, for example, a pulse motor. The actuator generates a driving force under the control of the controller 7. The movement mechanism 21a includes a mechanism that transmits the driving force output from the actuator to the first focusing lens. Here, the controller 7 automatically controls the actuator according to a predetermined computer program(s). Alternatively, the controller 7 controls the actuator based on operation signals from the operation unit 82 (a focusing operation unit 822) of the user interface 8. On the other hand, in the case of manual movement, the actuator is not required. In the case of manual movement, the user performs an operation for moving the first focusing lens by the use of the operation unit 82 (the focusing operation unit 822). A force F1', which is applied through this operation, is transmitted to the movement mechanism 21a via a mechanism (not shown). The movement mechanism 21a converts the transmitted force F1' into a force F2' that is for moving the first focusing lens.

Similarly, the imaging optical system 22 includes a movement mechanism 22a which is for moving a second focusing lens (not shown) that changes the focal position of the imaging optical system 22 in the optical axis direction thereof. The second focusing lens includes one or more lenses. The second focusing lens moves electrically and/or manually. In the case of electric movement, the movement mechanism 22a includes an actuator. The actuator includes, for example, a pulse motor. The actuator generates a driving force under the control of the controller 7. The movement mechanism 22a includes a mechanism that transmits the driving force output from the actuator to the second focusing lens. Here, the controller 7 automatically controls the actuator according to a predetermined computer program(s). Alternatively, the controller 7 controls the actuator based on operation signals from the operation unit 82 (the focusing operation unit 822) of the user interface 8. On the other hand, in the case of manual movement, the actuator is not required. In the case of manual movement, the user performs an operation for moving the second focusing lens by the use of the operation unit 82 (the focusing operation unit 822). A force F1", which is applied through this operation, is transmitted to the movement mechanism 22a via a mechanism (not shown). The movement mechanism 22a converts the transmitted force F1' into a force F2" that is for moving the second focusing lens.

The controller 7 includes, for example, a microprocessor, a RAM, a ROM, a hard disk drive, a programmable logic device, a communication interface, and the like. The controller 7 performs various kinds of controls of the ophthalmic apparatus 1. For example, the controller 7 performs control of the interference optical system 21, control of the imaging optical system 22, control of the movement mechanism 5 (the actuator therein), control of an information output unit 81, and the like. When the attachment unit 4 includes a controllable component(s), the controller 7 can control the component(s).

Further, the controller 7 may include a function as an image forming unit and/or as an image processor. For example, the controller 7 is configured to form image data of a cross sectional image of the subject's eye E, based on detection signals of interference light output from the detector of the interference optical system 21. As with conventional spectral domain OCT, such image forming processing includes, for example, noise removal (noise reduction), filtering, Fast Fourier Transform (FFT). When another type of OCT is employed, the controller 7 executes a known processing according to the type of OCT. In addition, the controller 7 may be configured to receive image data of the subject's eye E obtained by the imaging optical system 22, and to perform predetermined image processing on the image data.

The controller 7 stores various kinds of data. The data stored in the controller 7 includes, for example, data acquired by the interference optical system 21 (examination data, image data), image data acquired by the imaging optical system 22, subject information, subject's eye information, and the like. The controller 7 also stores various kinds of computer programs and data for operating the ophthalmic apparatus 1.

The user interface 8 includes the information output unit 81 and the operation unit 82. The information output unit 81 includes a display device, an audio output device, a printing device, or the like. The information output unit 81 operates under the control of the controller 7. The operation unit 82 is used by the user to operate the ophthalmic apparatus 1. Further, the operation unit 82 is used for inputting information to the ophthalmic apparatus 1. The operation unit 82 includes an optical system operation unit 821. The optical system operation unit 821 includes the focusing operation unit 822 for carrying out focusing of the optical system 20 with respect to the subject's eye E. The operation unit 82 may include various kinds of buttons, keys, and levers provided on the housing of the ophthalmic apparatus 1 or the outside thereof. The information output unit 81 and the operation unit 82 need not be configured as separate devices. For example, a device like a touch panel, which has both a display function integrated and an operation function, may be employed. The information output unit 81 is an example of a "display device" according to the present embodiment.

The operation unit 82 is used by the user to designate an imaging mode of the ophthalmic apparatus 1. In the present embodiment, the imaging mode includes at least a fundus imaging mode for imaging the fundus Ef and an anterior segment imaging mode for imaging the anterior segment Ea. The ophthalmic apparatus 1 is capable of performing OCT for the fundus Ef when the attachment unit 4 is not attached to the ophthalmic apparatus 1. On the other hand, when the attachment unit 4 is attached to the ophthalmic apparatus 1, the ophthalmic apparatus 1 can perform OCT for the anterior segment Ea. In summary, the ophthalmic apparatus 1 is used for imaging the anterior segment Ea in the first state in which the attachment unit 4 is attached, and is used for imaging the fundus Ef in the second state in which the attachment unit 4 is not attached.

The optical system operation unit 821 is used by the user to operate the optical system 20. The operation of the optical system 20 includes, for example, the following operations: operation for changing the focal position of the interference optical system 21; operation for changing the length of the optical path for the OCT measurement in the interference optical system 21; operation for changing the focal position of the imaging optical system 22; operation for switching light sources (e.g., wavelengths) of the interference optical system 21 or of the imaging optical system 22; and operation for inserting/removing a predetermined optical member(s) into/from the optical path of the interference optical system 21 or of the imaging optical system 22. The user performs operation for changing the focal position of the interference optical system 21 and/or the focal position of the imaging optical system 22 by the use of the focusing operation unit 822. Upon receiving a signal from the optical system operation unit 821, the controller 7 controls the optical system 20 according to the imaging mode currently being performed.

Figure 2:
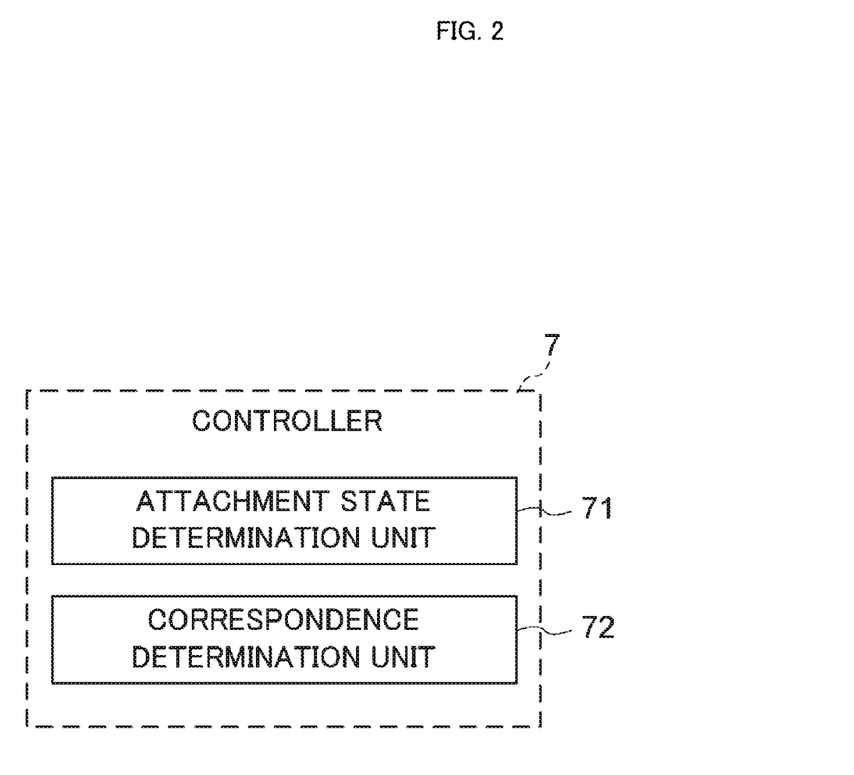
FIG. 2 is a schematic diagram illustrating an example of the configuration of the ophthalmic apparatus according to the embodiment.

FIG. 2 shows a functional block diagram of a configuration example of the controller 7 in FIG. 1. The controller 7 includes an attachment state determination unit 71 and a correspondence determination unit 72.

The attachment state determination unit 71 determines whether or not the attachment unit 4 is attached to the optical unit 2. As a specific example of the determination, the attachment state determination unit 71 receives the detection result of the attachment state of the attachment unit 4 from the attachment unit detector 41, and determines based on the detection result whether or not the attachment unit 4 is attached to the optical unit 2. It should be noted that when the attachment unit detector 41 is not provided, the following processing may be performed. First, the information output unit 81 inquires of the user whether or not the attachment unit 4 is attached. The attachment state determination unit 71 receives the content of answer as the content of operation for the operation unit 82. Based on the content of operation, the attachment state determination unit 71 determines whether or not the attachment unit 4 is attached to the optical unit 2.

The correspondence determination unit 72 determines whether or not the correspondence between the imaging mode designated using the operation unit 82 and the attachment state of the attachment unit 4 obtained by the attachment state determination unit 71 is appropriate. A storage unit (not shown) of the controller 7 stores in advance table information showing correspondences between imaging modes and attachment states of the attachment unit 4 (see FIG. 3). Based on the table information, the correspondence determination unit 72 is capable of determining whether or not the correspondence between the designated imaging mode and the attachment state of the attachment unit 4 is appropriate.

Figure 3:
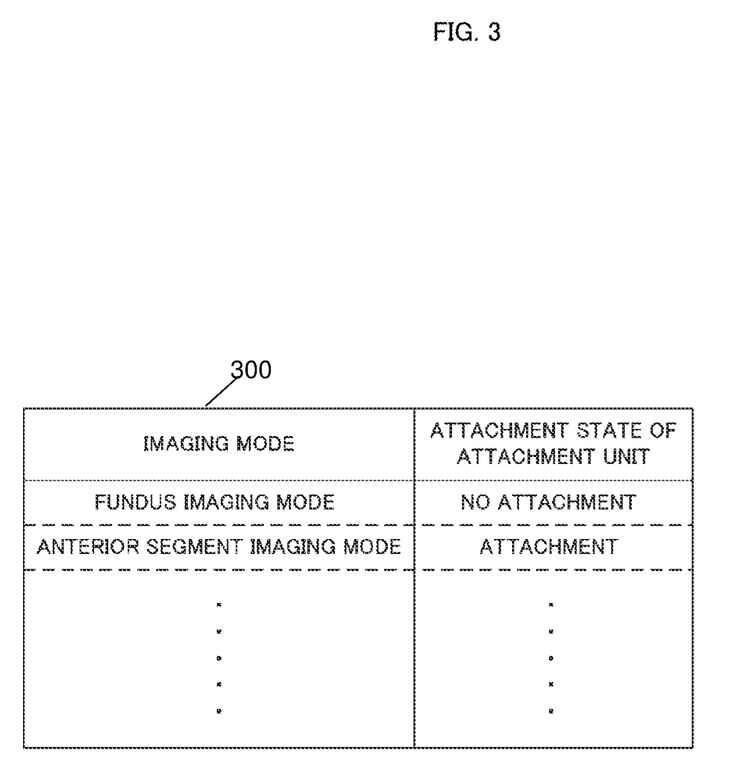
FIG. 3 is an explanatory diagram of the operation of the ophthalmic apparatus according to the embodiment.

For example, when the imaging mode designated using the operation unit 82 is the fundus imaging mode and the attachment state determination unit 71 has determined that the attachment unit 4 is not attached to the optical unit 2, the correspondence determination unit 72 determines, based on the table information shown in FIG. 3, that the correspondence between the imaging mode and the attachment state of the attachment unit 4 is appropriate. On the other hand, when the imaging mode designated using the operation unit 82 is the fundus imaging mode and the attachment state determination unit 71 has determined that the attachment unit 4 is attached to the optical unit 2, the correspondence determination unit 72 determines, based on the table information shown in FIG. 3, that the correspondence between the imaging mode and the attachment state of the attachment unit 4 is not appropriate.

Further, when the imaging mode designated using the operation unit 82 is the anterior segment imaging mode and the attachment state determination unit 71 has determined that the attachment unit 4 is not attached to the optical unit 2, the correspondence determination unit 72 determines, based on the table information shown in FIG. 3, that the correspondence between the imaging mode and the attachment state of the attachment unit 4 is not appropriate. On the other hand, when the imaging mode designated using the operation unit 82 is the anterior segment imaging mode and the attachment state determination unit 71 has determined that the attachment unit 4 is attached to the optical unit 2, the correspondence determination unit 72 determines, based on the table information shown in FIG. 3, that the correspondence between the imaging mode and the attachment state of the attachment unit 4 is appropriate.

When the correspondence determination unit 72 has determined that the correspondence between the imaging mode and the attachment state of the attachment unit 4 is appropriate, the controller 7 controls at least the optical system 20. An example of the control includes preparation control for imaging in a designated imaging mode such as control of the positions of the optical elements in the optical system 20 according to the designated imaging mode. Further, an example of the control includes commencement control for imaging. Examples of the preparation control for imaging include the followings: control for moving the optical element to a predetermined focal position of the interference optical system 21; control for moving the optical element to a predetermined focal position of the imaging optical system 22; control for setting the optical path length of the measurement light to a predetermined length; control for setting the optical path length of the reference light to a predetermined length; control of optical elements according to various parameters received in relation to the designated imaging mode; and control for switching light sources or for changing wavelengths to be used. An example of the commencement control of imaging includes control for displaying a screen for causing the user to provide an instruction for commencement of imaging on the information output unit 81.

When the correspondence determination unit 72 has determined that the correspondence between the imaging mode and the attachment state of the attachment unit 4 is not appropriate, the controller 7 performs control for prohibiting imaging in at least the designated imaging mode. For example, the control for prohibiting imaging includes a display control for displaying notifying information on the information output unit 81. Examples of the notifying information include the followings: information for notifying the mismatch between the imaging mode and the attachment state of the attachment unit 4; information for prompting the user to switch the imaging mode; and information for prompting the user to change the attachment state of the attachment unit 4.

It should be noted that after the correspondence determination unit 72 has determined that the correspondence between the imaging mode and the attachment state of the attachment unit 4 is not appropriate, the correspondence determination unit 72 can again determine whether or not the correspondence between the imaging mode and the attachment state of the attachment unit 4 is appropriate.

When the correspondence determination unit 72 has determined that the new correspondence is appropriate, the controller 7 releases the imaging prohibition in the designated imaging mode. The re-determination of whether or not the correspondence is appropriate can be performed at predetermined time intervals as will be described later. Alternatively, the timing of the re-determination of the correspondence and the timing of the determination performed by the attachment state determination unit 71 may be synchronized. In another example, the re-determination may be performed in response to the fact that the user performing a predetermined operation.

As a result, cases as the followings can be prevented: a case of performing imaging in the anterior segment imaging mode in the state where the attachment unit 4 is not attached; and a case of performing imaging in the fundus imaging mode in a state where the attachment unit 4 is attached. Consequently, this can prevent a situation in which the subject's eye E is imaged in an inappropriate imaging mode.

Figure 4:
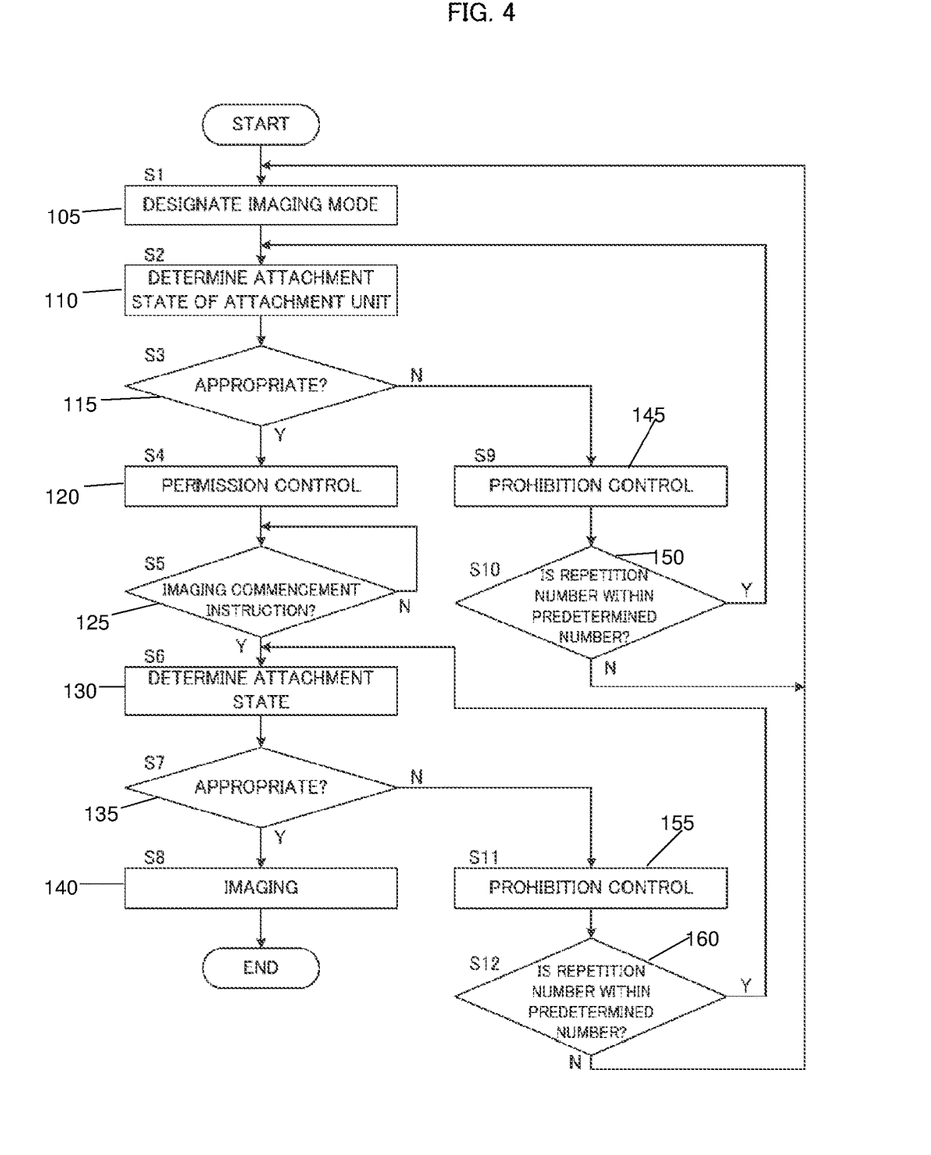
FIG. 4 is a flowchart illustrating an example of the operation of the ophthalmic apparatus according to the embodiment.

The operation of the ophthalmic apparatus 1 will be described. FIG. 4 shows an example of the operation of the ophthalmic apparatus 1.

First, at step 105 (S1), the controller 7 monitors imaging mode designation performed using the operation unit 82, and receives the imaging mode designated by the user.

Next, at step 110 (S2), the attachment state determination unit 71 of the controller 7 determines whether or not the attachment unit 4 is attached to the optical unit 2.

Next, at step 115 (S3), by referring to the table information 300 shown in FIG. 3, for example, the correspondence determination unit 72 of the controller 7 determines whether or not the correspondence between the imaging mode designated in S1 and the attachment state of the attachment unit 4 determined in S2 is appropriate. When the correspondence determination unit 72 has determined that the correspondence between the imaging mode and the attachment state of the attachment unit 4 is appropriate (S3: Y), the control by the controller 7 proceeds to S4. On the other hand, when the correspondence determination unit 72 has determined that the correspondence between the imaging mode and the attachment state of the attachment unit 4 is not appropriate (S3: N), the control by the controller 7 proceeds to S9.

When the correspondence determination unit 72 has determined that the correspondence between the imaging mode and the attachment state of the attachment unit 4 is appropriate in S3 (S3: Y), the controller 7 performs control for permission to carry out imaging in the designated imaging mode. Such imaging permission control includes, for example, control of the positions of the optical elements in the optical system 20 in order to perform imaging in the designated imaging mode. In addition, the operation unit 82 may be used to set various parameters to perform imaging in the designated imaging mode. Further, the controller 7 can control the optical system 20 according to the various parameters set using the operation unit 82.

In step 120 (S4), the controller 7 can perform, for example, the following controls. When imaging in the fundus imaging mode is permitted based on the determination result obtained by the correspondence determination unit 72 in S3, the controller 7 can change both the focal position of the imaging optical system 22 and the focal position of the interference optical system 21 based on the operation performed using the focusing operation unit 822. On the other hand, when imaging in the anterior segment imaging mode is permitted in S3, the controller 7 can prohibit change of the focal position of the interference optical system 21. In addition, the controller 7 can change the focal position of the imaging optical system 22 in response to the operation performed using the focusing operation unit 822. In summary, the controller 7 can change both the focal position of the imaging optical system 22 and the focal position of the interference optical system 21 when the focusing operation unit 822 is operated while the fundus imaging mode is being performed, and can change only the focal position of the imaging optical system 22 when the focusing operation unit 822 is operated while the anterior segment imaging mode is being performed. In this manner, the contents of control of the optical system 20 in response to the same operation performed using the focusing operation unit 822 can be switched according to the imaging mode designated. This, as a result, can improve the operability according to the imaging mode.

Next, at step 125 (S5), the controller 7 monitors whether or not the user has issued an instruction for commencement of imaging in the imaging mode designated in S1 by the use of the operation unit 82 (S5: N). When the user issues imaging commencement instruction using the operation unit 82 (S5: Y), the control by the controller 7 proceeds to S6.

When the user issues imaging commencement instruction using the operation unit 82 (S5: Y), the attachment state determination unit 71 of the controller 7 determines, at step 130 (S6), whether or not the attachment unit 4 is attached to the optical unit 2, as in S2.

Next, as in S3, the correspondence determination unit 72 of the controller 7 refers to the table information shown in FIG. 3 and determines whether or not the correspondence between the imaging mode designated in S1 and the attachment state of the attachment unit 4 determined in S6 is appropriate, at step 135 (S7). S7 is performed in order to prevent a situation in which an inappropriate imaging mode is still applied even though the attachment state of the attachment unit 4 has been changed after the designation of the imaging mode in S1. When the correspondence determination unit 72 has determined that the correspondence between the imaging mode and the attachment state of the attachment unit 4 is appropriate (S7: Y), the control by the controller 7 proceeds to S8. On the other hand, when the correspondence determination unit 72 has determined that the correspondence between the imaging mode and the attachment state of the attachment unit 4 is not appropriate (S7: N), the control by the controller 7 proceeds to S11.

At step 140 (S8), the controller 7 performs control for imaging of the subject's eye E with the imaging mode designated in S1 and in the state of the optical system 20 controlled in S4.

When the correspondence determination unit 72 has determined that the correspondence between the imaging mode designated in S1 and the attachment state of the attachment unit 4 determined in S2 is not appropriate in S3 (S3: N), the controller 7 performs imaging prohibition control, at step 145 (S9), for prohibiting imaging in the imaging mode designated in S1. An example of the imaging prohibition control includes a display control for displaying the notifying information on the information output unit 81. The notifying information includes information such as prompting the user to change the attachment state of the attachment unit 4 as described above.

At step 150 (S10), when the number of repetitions of the imaging prohibition control in S9 is equal to or less than a predetermined number (S10: Y), the control by the controller 7 proceeds to S2. As a result, prohibition of imaging in the imaging mode designated in S1 can be released at a stage before the number of repetitions of the imaging prohibition control reaches the predetermined number. On the other hand, when the number of repetitions of the imaging prohibition control in S9 exceeds the predetermined number (S10: N), the control by the controller 7 proceeds to S1.

In the case of releasing the imaging prohibition in the imaging mode designated in S1, the control by the controller 7 may be shifted from S10 to S2 when a predetermined time has elapsed. Alternatively, the control by the controller 7 may be shifted from S10 to S2 in synchronization with the timing of new determination performed by the attachment state determination unit 71.

When the correspondence determination unit 72 has determined that the correspondence between the imaging mode and the attachment state of attachment unit 4 is not appropriate in S7 (S7: N), the controller 7 performs imaging prohibition control, at step 155 (S11), for prohibiting imaging in the imaging mode designated in S1. The imaging prohibition control includes, as in S9, a display control for displaying the notifying information on the information output unit 81.

At step 160 (S12), when the number of repetitions of the imaging prohibition control in S11 is equal to or less than a predetermined number (S12: Y), the control by the controller 7 proceeds to S6. As a result, prohibition of imaging in the imaging mode designated in S1 can be released at a stage before the number of repetitions of the imaging prohibition control reaches the predetermined number. On the other hand, when the number of repetitions of the imaging prohibition control in S11 exceeds the predetermined number (S12: N), the control by the controller 7 proceeds to S1.

In the case of releasing the imaging prohibition in the imaging mode designated in S1, the control by the controller 7 may be shifted from S12 to S6 when a predetermined time has elapsed. Alternatively, the control by the controller 7 may be shifted from S12 to S6 in synchronization with the timing of new determination performed by the attachment state determination unit 71.

The effects of the ophthalmic apparatus 1 will be described.

The ophthalmic apparatus is capable of selectively performing: imaging in the fundus imaging mode (the first imaging mode) in which imaging of the subject's eye is performed in the first state where the attachment unit 4 is not attached; and imaging in the anterior segment imaging mode (the second imaging mode) in which imaging of the subject's eye is performed in the second state where the attachment unit is attached. The ophthalmic apparatus includes the operation unit 82, the attachment state determination unit 71, the correspondence determination unit 72, and the controller 7. The operation unit 82 is configured for designating an imaging mode. The attachment state determination unit 71 is configured to determine whether or not the attachment unit 4 is attached. The correspondence determination unit 72 is configured to determine whether or not the correspondence between the imaging mode designated using the operation unit 82 and the attachment state of the attachment unit 4 obtained by the attachment state determination unit 71 is appropriate. The controller 7 is configured to perform control for prohibiting imaging in at least the designated imaging mode when the correspondence determination unit 72 has determined that the correspondence is not appropriate.

According to such a configuration, it is possible to determine before imaging whether or not the correspondence between the designated imaging mode and the attachment state of the attachment unit is appropriate. Further, when the correspondence has been determined to be not appropriate, control can be performed to prohibit imaging in the designated imaging mode. Thereby, it is possible to prevent imaging of the subject's eye E in an inappropriate imaging mode.

After the correspondence determination unit 72 has determined that the correspondence between the imaging mode and the attachment state of the attachment unit is not appropriate, the correspondence determination unit 72 can again determine whether or not the correspondence between the imaging mode and the attachment state of the attachment unit is appropriate. When the correspondence determination unit 72 has determined that the new correspondence is appropriate, the controller 7 can release the imaging prohibition in the designated imaging mode.

According to such a configuration, when the attachment state of the attachment unit corresponding to the designated imaging mode has been determined to be not appropriate, and further, when the control to prohibit the imaging in the imaging mode has been performed, it is possible to release the imaging prohibition state by performing re-determination with the correspondence determination unit 72. With this, even when the imaging prohibition control has been performed as a result of the user trying to image the subject's eye E in an inappropriate imaging mode, imaging the subject's eye E in a desired imaging mode can be achieved by changing one or both of the imaging mode and the attachment state of the attachment unit 4.

The ophthalmic apparatus 1 may include the optical system 20 for imaging the subject's eye. Further, when the correspondence determination unit 72 has determined that the correspondence between the imaging mode and the attachment state of the attachment unit is appropriate, the controller 7 can control the optical system 20 according to the designated imaging mode.

According to such a configuration, when the correspondence between the imaging mode and the attachment state of the attachment unit has been determined to be appropriate, control such as preparation for imaging in the imaging mode can be performed. Thereby, it is possible to provide the ophthalmic apparatus 1 that is convenient for the user.

The control for prohibiting imaging may include a display control for displaying the notifying information on the information output unit 81 (the display device).

According to such a configuration, it is possible to inform the user in advance of imaging the subject's eye E in an inappropriate imaging mode.

The attachment unit 4 may be an optical attachment unit for imaging the anterior segment. Further, the first imaging mode may be the fundus imaging mode, and the second imaging mode may be the anterior segment imaging mode.

According to such a configuration, it is possible to prevent imaging in the anterior segment imaging mode in a state in which the attachment unit 4 for imaging the anterior segment is not attached. Further, it is possible to prevent imaging in the fundus imaging mode in a state in which the attachment unit 4 for imaging the anterior segment is attached. Thereby, imaging of the subject's eye E in an inappropriate imaging mode can be prevented.

The ophthalmic apparatus 1 may include the optical system 20 for imaging the subject's eye E and the optical system operation unit 821 for operating the optical system 20. Further, the controller 7 may be configured to control the optical system 20 according to the currently performed imaging mode upon receiving a signal input from the optical system operation unit 821.

According to such a configuration, the content of the operation of the optical system 20 performed using the optical system operation unit 821 can be changed according to the imaging mode designated by the use of the operation unit 82. As a result, it is possible to operate the optical system 20 in accordance with the imaging mode. Therefore, the operability of the ophthalmic apparatus 1 is improved.

The ophthalmic apparatus 1 may be capable of performing at least the fundus imaging mode and the anterior segment imaging mode. Further, the optical system 20 may include the imaging optical system for imaging (photographing) the fundus Ef of the subject's eye E and the interference optical system 21 for acquiring information on the subject's eye E using OCT. In addition, the optical system operation unit 821 may include the focusing operation unit 822 for performing focusing of the optical system 20 with respect to the subject's eye E. Further, the controller 7 may be configured to change both the focal position of the imaging optical system 22 and the focal position of the interference optical system 21 when the focusing operation unit 822 is operated while the fundus imaging mode is being performed. The controller 7 may also be configured to change only the focal position of the imaging optical system 22 when the focusing operation unit 822 is operated while the anterior imaging mode is being performed.

According to such a configuration, in response to the same operation performed using the optical system operation unit 821, the contents of control of the optical system 20 can be switched according to the designated imaging mode. With this, the operability according to the imaging mode can be improved.

The first embodiment has described the case where imaging in the designated imaging mode is prohibited based on the result of determination of whether or not the correspondence between the designated imaging mode and the attachment state of the attachment unit 4 is appropriate. However, embodiments are not limited to this. In the second embodiment, imaging in the designated imaging mode is prohibited based on the result of determination of whether or not the correspondence between the designated imaging mode and the type of the attachment unit 4 is appropriate. Hereinafter, the ophthalmic apparatus according to the second embodiment will be described focusing on differences from the first embodiment.

To the optical unit of the ophthalmic apparatus according to the second embodiment, two or more attachment units corresponding to two or more imaging modes are selectively attached. For example, the two or more imaging modes include not only the fundus imaging mode and the anterior segment imaging mode, but also imaging modes for imaging arbitrary sites (e.g., the vitreous body, the crystalline lens, etc.) of the subject's eye. The attachment units are prepared for the respective imaging target sites, and these are selectively applied to the ophthalmic apparatus.

The ophthalmic apparatus according to the second embodiment includes a controller 7a in place of the controller 7 of the ophthalmic apparatus 1 according to the first embodiment.

Figure 5:
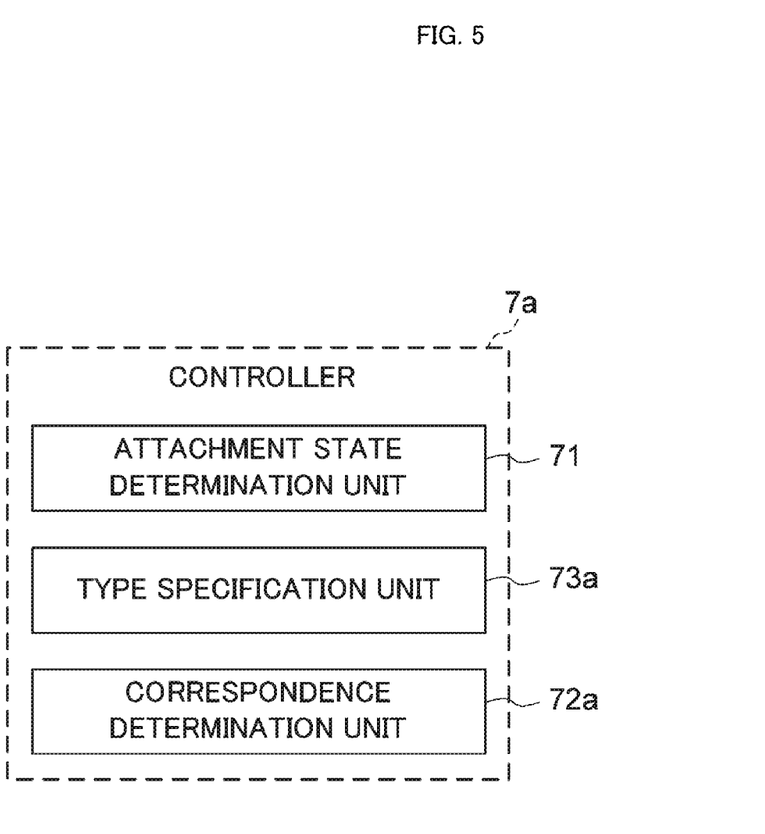
FIG. 5 is a schematic diagram describing the operation of the ophthalmic apparatus according to the embodiment.

FIG. 5 is a functional block diagram of a configuration example of the controller according to the second embodiment. In FIG. 5, components similar to those in FIG. 2 are given the same reference numerals. The description of such components is basically omitted. The controller 7a includes an attachment state determination unit 71, a correspondence determination unit 72a, and a type specification unit 73a.

The attachment state determination unit 71 determines whether or not the attachment unit 4 is attached to the optical unit 2.

When the attachment state determination unit 71 has determined that the attachment unit 4 is attached, the type specification unit 73a specifies the type of the attachment unit 4. Examples of the type of the attachment unit 4 include an attachment unit for imaging the anterior segment, an attachment unit for imaging the crystalline lens, and the like. For example, the type specification unit 73a specifies the type of the attachment unit 4 based on a predetermined physical quantity generated according to attachment (or detachment) of the attachment unit 4. The attachment unit detector 41 may be configured to detect the attachment state of the attachment unit 4 with a magnetic sensor. In this case, the type specification unit 73a may be configured to specify the type of the attachment unit 4, based on the strength (magnitude) of the magnetic force or on the variation (amount, direction) of the magnetic force generated in response to the attachment (or detachment) of the attachment unit 4. Alternatively, the attachment unit detector 41 may be configured to detect the attachment state of the attachment unit 4 with a pressure sensor. In this case, the type specification unit 73a may be configured to specify the type of the attachment unit 4 based on the pressure or on the variation of the pressure generated in response to the attachment (or detachment) of the attachment unit 4.

In another example, the attachment unit detector 41 includes a plurality of micro switches. The micro switches may be arranged so that different micro switches are turned on depending on types of the attachment unit 4 attached. In this case, the type specification unit 73a may be configured to specify the type of the attachment unit 4 by specifying one or more micro switches that have been turned on. In still another example, the type specification unit 73a may be configured to specify the type of attachment unit based on an image from a camera (for example, the cameras that perform stereoscopic imaging) included in the imaging optical system 22.

In the present embodiment, when the attachment state determination unit 71 has determined that the attachment unit 4 is not attached to the optical unit 2, the type specification unit 73a obtains specification result "no type" as the type of the attachment unit 4.

The correspondence determination unit 72a determines whether or not the correspondence between the imaging mode designated by the use of the operation unit 82 and the type of the attachment unit 4 specified by the type specification unit 73a is appropriate. A storage unit (not shown) of the controller 7a stores in advance table information showing correspondences between imaging modes and types of the attachment unit 4 (see FIG. 6). Based on the table information, the correspondence determination unit 72a determines whether or not the correspondence between the designated imaging mode and the type of the attachment unit 4 is appropriate.

Described below is a case in which the imaging mode designated by the use of the operation unit 82 is the fundus imaging mode and the specification result (the type of the attachment unit 4) obtained by the type specification unit 73a is "no type". Here, the case in which the specification result is "no type" corresponds to the case in which the attachment state determination unit 71 has determined that the attachment unit 4 is not attached to the optical unit 2. In this case, based on the table information 600 shown in FIG. 6, the correspondence determination unit 72a determines that the correspondence between the imaging mode and the type of the attachment unit 4 is appropriate. On the other hand, when the imaging mode designated by the use of the operation unit 82 is the fundus imaging mode and the type specification unit 73a has specified the type of the attachment unit 4 (that is, when the attachment state determination unit 71 has determined that the attachment unit 4 is attached to the optical unit 2), the correspondence determination unit 72a determines that the correspondence between the imaging mode and the type of the attachment unit 4 is not appropriate based on the table information 600 shown in FIG. 6.

Figure 6:
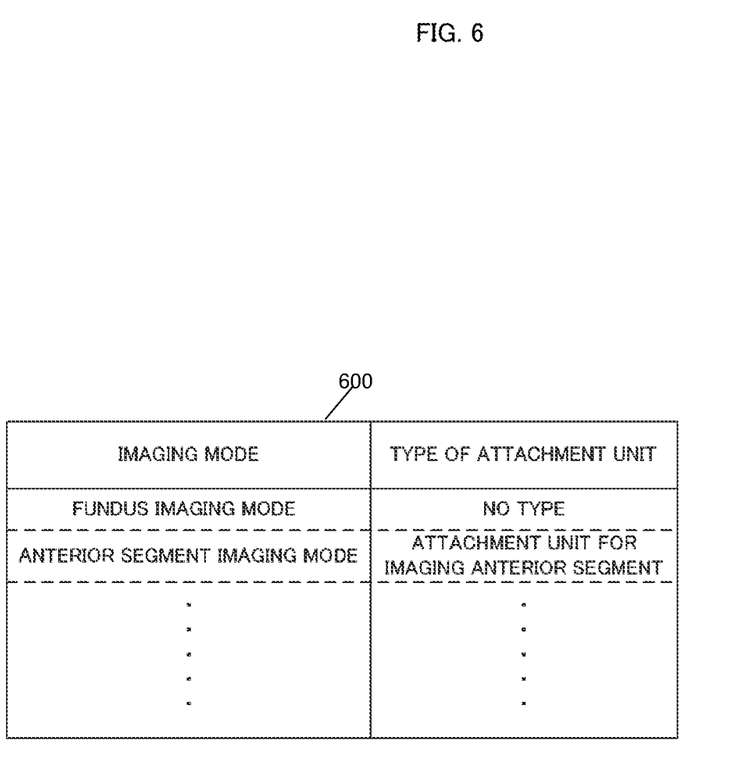
FIG. 6 is an explanatory diagram of the operation of the ophthalmic apparatus according to the embodiment.

When the imaging mode designated by the use of the operation unit 82 is the anterior segment imaging mode and the specification result obtained by the type specification unit 73a is "no type", the correspondence determination unit 72a determines, based on the table information shown in FIG. 6, that the correspondence between the imaging mode and the type of the attachment unit 4 is not appropriate. On the other hand, when the imaging mode designated by the use of the operation unit 82 is the anterior segment imaging mode and the type specification unit 73a has specified that the attachment unit 4 attached to the optical unit 2 is an attachment unit for imaging the anterior segment, the correspondence determination unit 72a determines that the correspondence between the imaging mode and the type of the attachment unit 4 is appropriate based on the table information shown in FIG. 6.

When the correspondence determination unit 72a has determined that the correspondence between the imaging mode and the type of the attachment unit 4 is appropriate, the controller 7a controls at least the optical system 20. As with the first embodiment, the control of the optical system 20 includes control for preparing imaging in a designated imaging mode, such as control of the positions of the optical elements in the optical system 20 corresponding to the designated imaging mode. Further, the control of the optical system 20 may include control for commencement of imaging.

When the correspondence determination unit 72a has determined that the correspondence between the imaging mode and the type of the attachment unit 4 is not appropriate, the controller 7a performs control for prohibiting imaging in at least the designated imaging mode. For example, the imaging prohibition control includes a display control for displaying the notifying information on the information output unit 81. Examples of the notifying information include the followings: information for notifying the mismatch between the imaging mode and the attachment state of the attachment unit 4; information for prompting the user to switch the imaging mode; and information for prompting the user to change the attachment state of the attachment unit 4.

It should be noted that after the correspondence determination unit 72a has determined that the correspondence between the imaging mode and the type of the attachment unit 4 is not appropriate, the correspondence determination unit 72a can again determine whether or not the correspondence between the imaging mode and the type of the attachment unit 4 is appropriate. When the correspondence determination unit 72a has determined that the new correspondence is appropriate, the controller 7a can release the prohibition of imaging in the designated imaging mode. The re-determination of whether or not the correspondence is appropriate may be performed at the timing when a predetermined time has elapsed as will be described later. Alternatively, the timing of the re-determination of whether or not the correspondence is appropriate may be synchronized with the timing of the determination performed by the attachment state determination unit 71 and/or the timing of the type specification performed by the type specification unit 73a.

With this, it is possible to prevent imaging in the anterior segment imaging mode in a state in which the attachment unit 4 of an inappropriate type is attached to the optical unit 2, for example. More generally, it is possible to prevent imaging of the subject's eye E in an inappropriate imaging mode or with an inappropriate attachment unit.

Figure 7:
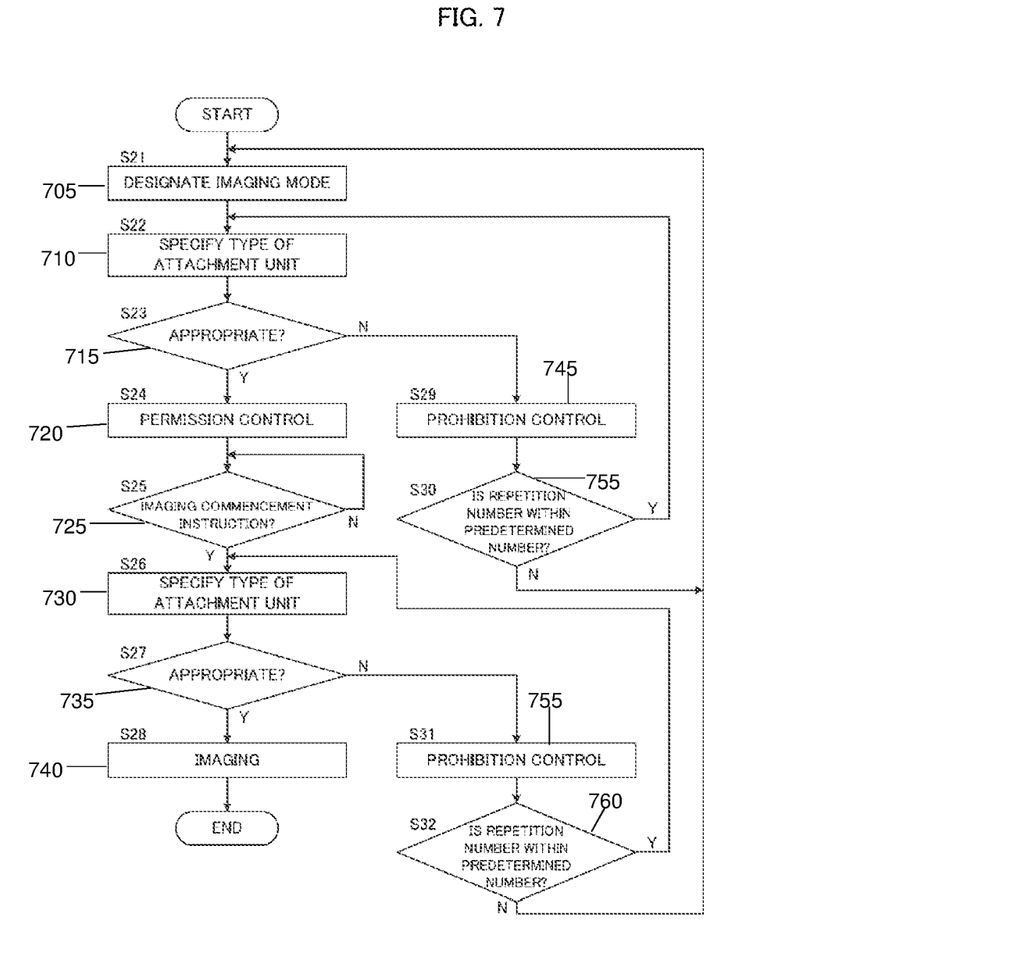
FIG. 7 is a flowchart illustrating an example of the operation of the ophthalmic apparatus according to the embodiment.

The operation of the ophthalmic apparatus according to the second embodiment will be described. FIG. 7 represents an example of the operation of the ophthalmic apparatus according to the present embodiment.

First, at step 705 (S21), the controller 7a monitors imaging mode designation of the imaging mode performed by the user with the use of the operation unit 82, and receives the imaging mode designated by the user with the use of the operation unit 82.

Next, at step 710, (S22), the attachment state determination unit 71 of the controller 7a determines whether or not the attachment unit 4 is attached to the optical unit 2. When the attachment state determination unit 71 has determined that the attachment unit 4 is attached to the optical unit 2, the type specification unit 73a of the controller 7a specifies the type of the attachment unit 4.

Next, at step 715 (S23), the correspondence determination unit 72a of the controller 7a refers to the table information shown in FIG. 6, for example, to determine whether or not the correspondence between the imaging mode designated in S21 and the type of the attachment unit 4 specified in S22 is appropriate. When the correspondence determination unit 72a has determined that the correspondence between the imaging mode and the type of the attachment unit 4 is appropriate (S23: Y), the control by the controller 7a proceeds to S24. On the other hand, when the correspondence determination unit 72 has determined that the correspondence between the imaging mode and the type of the attachment unit 4 is not appropriate (S23: N), the control by the controller 7a proceeds to S29.

When the correspondence determination unit 72a has determined that the correspondence between the imaging mode and the type of the attachment unit 4 is appropriate in S23 (S23: Y), the controller 7a performs control for permission to carry out imaging in the designated imaging mode. Such imaging permission control includes, for example, control of the positions of the optical elements in the optical system 20 for imaging in the designated imaging mode. In addition, the controller 7a can perform setting of various parameters for imaging in the designated imaging mode by the use of the operation unit 82. Further, the controller 7a can control the optical system 20 according to the various parameters set by the use of the operation unit 82.

For example, as in S4, the following control may be performed in step 720 (S24). When imaging in the fundus imaging mode has been permitted based on the determination result obtained by the correspondence determination unit 72a in S23, the controller 7a can change both the focal position of the imaging optical system 22 and the focal position of the interference optical system 21 based on the operation performed by the use of the focusing operation unit 822. On the other hand, when imaging in the anterior segment imaging mode has been permitted in S23, the controller 7a can prohibit the change of the focal position of the interference optical system 21 and can change the focal position of the imaging optical system 22 in response to the operation performed by the use of the focusing operation unit 822.

Next, at step 725 (S5), the controller 7a monitors whether or not the user has issued an instruction to commence imaging in the imaging mode designated in S21 by the use of the operation unit 82 (S25: N). When an instruction for commencement of imaging has been issued by the use of the operation unit 82 (S25: Y), the control by the controller 7a proceeds to step 730 S26.

When an instruction for commencement of imaging has been issued by the use of the operation unit 82 (S25: Y), the attachment state determination unit 71 of the controller 7a determines, as in S22, whether or not the attachment unit 4 is attached to the optical unit 2. When the attachment state determination unit 71 has determined that the attachment unit 4 is attached to the optical unit 2, the type specification unit 73a of the controller 7a specifies the type of the attachment unit 4.

Next, as in S23, the correspondence determination unit 72a of the controller 7a, for example, refers to the table information shown in FIG. 6 and determines whether or not the correspondence between the imaging mode designated in S21 and the type of the attachment unit 4 specified in S26 is appropriate. Step 735 (S27) is performed, as in S7, in order to prevent a situation in which an inappropriate imaging mode is still applied even though the type (including the attachment state) of the attachment unit 4 has been changed after the designation of the imaging mode in S21. When the correspondence determination unit 72a has determined that the correspondence between the imaging mode and the type of the attachment unit 4 is appropriate (S27: Y), the control by the controller 7a proceeds to S28. On the other hand, when the correspondence determination unit 72a has determined that the correspondence between the imaging mode and the type of the attachment unit 4 is not appropriate (S27: N), the control by the controller 7a proceeds to S31.

At step 740 (S28), the controller 7a performs control for imaging of the subject's eye E with the imaging mode designated in S21 and in the state of the optical system 20 controlled in S24.

When the correspondence determination unit 72a has determined that the correspondence between the imaging mode designated in S21 and the type of the attachment unit 4 specified in S22 is not appropriate in S23 (S23: N), the controller 7a performs, as in S9, imaging prohibition control, at step 745 (S29), for prohibiting imaging in the imaging mode designated in S21.

At step 750 (S30), when the number of repetitions of the imaging prohibition control in S29 is equal to or less than a predetermined number (S30: Y), the control by the controller 7a proceeds to S22. As a result, prohibition of imaging in the imaging mode designated in S21 can be released at a stage before the number of repetitions of the imaging prohibition control reaches the predetermined number. On the other hand, when the number of repetitions of the imaging prohibition control in S29 exceeds the predetermined number (S30: N), the control by the controller 7a proceeds to S21.

In the case of releasing the imaging prohibition in the imaging mode designated in S21, the control by the controller 7a may be shifted from S30 to S22 when a predetermined time has elapsed. Alternatively, the control by the controller 7a may be shifted from S30 to S22 in synchronization with the timing of new determination performed by the attachment state determination unit 71.

When the correspondence determination unit 72a has determined that the correspondence between the imaging mode and the attachment state of attachment unit 4 is not appropriate in S27 (S27: N), the controller 7a performs, as in S11, imaging prohibition control, at step 755 (S31), for prohibiting imaging in the imaging mode designated in S21.

At step 760 (S32), when the number of repetitions of the imaging prohibition control in S31 is equal to or less than a predetermined number (S32: Y), the control by the controller 7a proceeds to S26. As a result, prohibition of imaging in the imaging mode designated in S21 can be released at a stage before the number of repetitions of the imaging prohibition control reaches the predetermined number. On the other hand, when the number of repetitions of the imaging prohibition control in S31 exceeds the predetermined number (S32: N), the control by the controller 7a proceeds to S21.

In the case of releasing the imaging prohibition in the imaging mode designated in S21, the control by the controller 7a may be shifted from S32 to S26 when a predetermined time has elapsed. Alternatively, the control by the controller 7a may be shifted from S32 to S26 in synchronization with the timing of new determination performed by the attachment state determination unit 71 or with the timing of new type specification performed by the type specification unit 73a.

The effects of the ophthalmic apparatus according to the present embodiment will be described.

An ophthalmic apparatus according to the present embodiment performs imaging of the subject's eye in a state in which two or more attachment units corresponding to two or more imaging modes are selectively attached. The ophthalmic apparatus includes the operation unit 82, the type specification unit 73a, the correspondence determination unit 72a, and the controller 7a. The operation unit 82 is configured for designating an imaging mode. The type specification unit 73a is configured to specify a type of an attachment unit attached. The correspondence determination unit 72a is configured to determine whether or not the correspondence between the imaging mode designated by the use of the operation unit 82 and the type of the attachment unit obtained by the type specification unit 73a is appropriate. The controller 7a is configured to perform control for prohibiting imaging in at least the designated imaging mode when the correspondence determination unit 72a determines that the correspondence is not appropriate.

According to such a configuration, determination of whether or not the correspondence between the content of designation of the imaging mode and the type of the attachment unit is appropriate can be performed before imaging. Further, when the correspondence has been determined to be not appropriate, it is possible to control so as to prohibit imaging in the designated imaging mode. With this, it is possible to prevent imaging of the subject's eye E in an inappropriate imaging mode.

The configurations described above are mere examples for embodying or carrying out the present invention, and therefore susceptible to several modifications and variations (omission, substitution, addition, etc.), all coming within the scope of the invention.

For example, an analysis mode may be switched according to the attachment state of an attachment unit. In the case of performing an image analysis corresponding to an attachment unit to be attached, any of the above embodiments can be employed. An example of switching the analysis mode includes switching between a fundus analysis mode and an anterior segment analysis mode. In the fundus analysis mode, by analyzing OCT images and/or fundus images, the thickness of the retina, the shapes of the layers, the aspects of lesions (distribution of drusens, etc.), and the like, for example, are evaluated. In the anterior segment analysis mode, by analyzing OCT images and/or anterior segment images, the thickness of the cornea, the shape of the cornea, the corner angle, and the like are evaluated. In another example, a scan mode can be switched according to the attachment state of an attachment unit. In the case of acquiring scan images corresponding to an attachment unit to be attached, any of the above embodiments can be employed. Incidentally, an example of scan mode includes various scan patterns of measurement light for acquiring OCT images.

There is an attachment unit which includes an optical member for changing the angle of view. In the case of switching the imaging angle of view (a normal angle of view mode, a wide angle imaging mode, etc.) according to the attachment state of the attachment unit, any of the above embodiments can be employed. Alternatively, there is an attachment unit which includes an optical member according to the refractive power of the subject's eye. In the case of switching the refractive power (a normal eye imaging mode, a (super) excessive myopic imaging mode, etc.) to be applied to the subject's eye in accordance with the attachment state of the attachment unit, any of the above embodiments can be employed.

Aspects of the designation of the imaging mode are not limited to the operation for designating the imaging mode itself. For example, the disease name and the imaging mode can be associated with each other in advance. In this case, it is possible to select (automatically) the imaging mode associated with the designated disease name in response to the operation of designating the disease name related to the diagnosis (or treatment). There is a disease associated with a plurality of imaging modes. In such a case, it is possible to rank two or more imaging modes in terms of priority in the order of selection. For example, in the diagnosis of glaucoma, both the fundus (the optic disc, etc.) and the anterior segment (the corner angle, etc.) may be considered. It is assumed that the fundus imaging mode and the anterior segment imaging mode are associated with the glaucoma mode, "priority 1" is assigned to the fundus imaging mode, and "priority 2" is assigned to the anterior segment imaging mode. In such a case, when the glaucoma mode is designated, the fundus imaging mode to which "priority 1" has been assigned is first selected. In this case, the operation of designation of the glaucoma mode corresponds to the designation of the fundus imaging mode. Further, an end trigger of the fundus imaging mode or a start trigger of the anterior segment imaging mode can be regarded as a designation of the anterior segment imaging mode.

The invention claimed is:

1. An ophthalmic apparatus that selectively performs a first imaging mode in which imaging of a subject's eye is performed in the first imaging mode, the first imaging mode being performed in a first state where an attachment unit is not attached, and selectively performs a second imaging mode in which imaging of the subject's eye is performed in the second imaging mode, wherein the second imaging mode differs from the first imaging mode, the second imaging mode being performed in a second state in which the attachment unit is attached, and capable of performing at least a fundus imaging mode and an anterior segment imaging mode, wherein the ophthalmic apparatus comprises:
an operation unit configured for designating an imaging mode as selected by a user of the operation unit;
an attachment state determination unit configured to determine whether or not the attachment unit is attached;
a correspondence determination unit configured to determine whether or not correspondence between the imaging mode designated by the user of the operation unit and an attachment state of the attachment unit obtained by the attachment state determination unit is appropriate;
an optical system configured to image the subject's eye;
an optical system operation unit configured for operating the optical system;
a controller configured to perform control for prohibiting imaging in at least the designated imaging mode when the correspondence determination unit has determined that the correspondence is not appropriate, and to control the optical system according to an imaging mode currently performed when receiving a signal input from the optical system operation unit, wherein the optical system comprises:
an imaging optical system configured to image a fundus of the subject's eye; and
an interference optical system configured to acquire information on the subject's eye with optical coherence tomography, and
the optical system operation unit comprises a focusing operation unit configured to perform focusing of the optical system with respect to the subject's eye, and
the controller is configured to move focal positions of both the imaging optical system and the interference optical system when the focusing operation unit is operated while the fundus imaging mode is being performed, and to move only the focal position of the imaging optical system when the focusing operation unit is operated while the anterior segment imaging mode is being performed.

2. The ophthalmic apparatus of claim 1, wherein after the correspondence determination unit has determined that the correspondence is not appropriate, the correspondence determination unit again determines whether or not the correspondence is appropriate, and in a case where it has been determined that the correspondence is appropriate, the controller releases prohibition of imaging in the designated imaging mode.

3. The ophthalmic apparatus of claim 1, wherein
when the correspondence determination unit has determined that the correspondence is appropriate, the controller controls the optical system according to the designated imaging mode.

4. The ophthalmic apparatus of claim 1, wherein the control for prohibiting imaging comprises display control for displaying notifying information on a display device.

5. The ophthalmic apparatus of claim 1, wherein
the attachment unit is an optical attachment unit for imaging an anterior segment,
the first imaging mode is the fundus imaging mode, and
the second imaging mode is the anterior segment imaging mode.

6. An ophthalmic apparatus performing imaging of a subject's eye in a state in which two or more attachment units corresponding to two or more imaging modes are selectively attached and capable of performing at least a fundus imaging mode and an anterior segment imaging mode, wherein the ophthalmic apparatus comprises:
an operation unit configured for designating an imaging mode;
a type specification unit configured to specify a type of an attachment unit attached;
a correspondence determination unit configured to determine whether or not correspondence between the imaging mode designated by a use of the operation unit and the type of the attachment unit obtained by the type specification unit is appropriate;

a controller configured to perform control for prohibiting imaging in at least the designated imaging mode when the correspondence determination unit has determined that the correspondence is not appropriate;
an optical system configured to image the subject's eye;
an optical system operation unit configured for operating the optical system, wherein the controller controls the optical system according to an imaging mode currently performed when receiving a signal input from the optical system operation unit; and wherein
the optical system comprises:
  an imaging optical system configured to image a fundus of the subject's eye; and
  an interference optical system configured to acquire information on the subject's eye with optical coherence tomography, and
the optical system operation unit comprises a focusing operation unit configured to perform focusing of the optical system with respect to the subject's eye, and
the controller is configured to move focal positions of both the imaging optical system and the interference optical system when the focusing operation unit is operated while the fundus imaging mode is being performed, and to move only the focal position of the imaging optical system when the focusing operation unit is operated while the anterior segment imaging mode is being performed.

7. The ophthalmic apparatus of claim 6, wherein after the correspondence determination unit has determined that the correspondence is not appropriate, the correspondence determination unit again determines whether or not the correspondence is appropriate, and in a case where it has been determined that the correspondence is appropriate, the controller releases prohibition of imaging in the designated imaging mode.

8. The ophthalmic apparatus of claim 6, wherein
when the correspondence determination unit has determined that the correspondence is appropriate, the controller controls the optical system according to the designated imaging mode.

9. The ophthalmic apparatus of claim 6, wherein the control for prohibiting imaging comprises display control for displaying notifying information on a display device.

* * * * *

UNITED STATES PATENT AND TRADEMARK OFFICE
CERTIFICATE OF CORRECTION

PATENT NO. : 10,231,620 B2
APPLICATION NO. : 15/514609
DATED : March 19, 2019
INVENTOR(S) : Ryota Ishiai et al.

It is certified that error appears in the above-identified patent and that said Letters Patent is hereby corrected as shown below:

On the Title Page

Item (72), Line 1, the residence information for inventor Ryota Ishiai "Tokyo (JP);" should read --Kita-ku, Tokyo (JP)--;

Item (72), Lines 1 and 2, the residence information for inventor Kota Fujii "Toda (JP)" should read --Toda-shi, Saitama (JP)--;

Item (72), Lines 2 and 3, the residence information for inventor Shigeru Okikawa "Tokyo (JP)" should read --Kita-ku, Tokyo (JP)--.

Signed and Sealed this
Ninth Day of July, 2019

Andrei Iancu
*Director of the United States Patent and Trademark Office*